US009358363B2

(12) United States Patent
Boulais

(10) Patent No.: US 9,358,363 B2
(45) Date of Patent: *Jun. 7, 2016

(54) MULTIPLE LUMEN ASSEMBLY FOR USE IN ENDOSCOPES OR OTHER MEDICAL DEVICES

(75) Inventor: Dennis R. Boulais, Danielson, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 397 days.

This patent is subject to a terminal disclaimer.

(21) Appl. No.: 13/477,508

(22) Filed: May 22, 2012

(65) Prior Publication Data
US 2012/0232526 A1 Sep. 13, 2012

Related U.S. Application Data

(63) Continuation of application No. 11/407,434, filed on Apr. 20, 2006, now Pat. No. 8,202,265.

(51) Int. Cl.
A61M 25/00 (2006.01)
A61B 1/005 (2006.01)
A61B 1/012 (2006.01)
A61B 1/018 (2006.01)

(52) U.S. Cl.
CPC .......... A61M 25/0026 (2013.01); A61B 1/0055 (2013.01); A61B 1/012 (2013.01); A61B 1/018 (2013.01); A61M 2025/004 (2013.01); A61M 2025/0034 (2013.01); A61M 2025/0036 (2013.01); A61M 2025/0039 (2013.01)

(58) Field of Classification Search
CPC ................. A61M 25/0026; A61M 2025/0034; A61M 2025/0036; A61M 2025/0039; A61M 2025/004

USPC .......... 604/27, 43, 93.01, 264, 265, 523, 524, 604/525
See application file for complete search history.

(56) References Cited

U.S. PATENT DOCUMENTS

| 2,916,055 A * | 12/1959 | Brumbach ................ F16L 9/00 138/111 |
| 3,266,059 A | 8/1966 | Stelle |
| 3,470,876 A | 10/1969 | Barchilon |
| 3,526,086 A | 9/1970 | Morgan |
| 3,572,325 A | 3/1971 | Bazell et al. |
| 3,581,738 A | 6/1971 | Moore |
| 4,108,211 A | 8/1978 | Tanaka |
| 4,286,585 A | 9/1981 | Ogawa |
| 4,294,162 A | 10/1981 | Fowler et al. |

(Continued)

FOREIGN PATENT DOCUMENTS

| DE | 87 14 480 U1 | 4/1988 |
| DE | 39 16 288 A1 | 11/1989 |

(Continued)

Primary Examiner — Kevin C Sirmons
Assistant Examiner — Shefali Patel
(74) Attorney, Agent, or Firm — Bookoff McAndrews, PLLC

(57) ABSTRACT

An endoscope or other medical device includes a number of lumens positioned in an outer shaft. The lumens are formed as a multiple lumen assembly. In one embodiment, individual lumens are connected to each other with a sheet or webbing material. The lumen assembly is rolled or folded along its length for incorporation into the outer shaft of the endoscope or the medical device. The sheet or webbing material may be notched or perforated to facilitate folding the lumen assembly and/or separating the individual lumens from the lumen assembly.

20 Claims, 6 Drawing Sheets

(56) References Cited

U.S. PATENT DOCUMENTS

| | | | |
|---|---|---|---|
| 4,311,134 | A | 1/1982 | Mitsui et al. |
| 4,315,309 | A | 2/1982 | Coli |
| 4,351,323 | A | 9/1982 | Ouchi et al. |
| 4,369,768 | A | 1/1983 | Vukovic |
| 4,425,113 | A | 1/1984 | Bilstad |
| 4,432,349 | A | 2/1984 | Oshiro |
| 4,471,766 | A | 9/1984 | Terayama |
| 4,473,841 | A | 9/1984 | Murakoshi et al. |
| 4,488,039 | A | 12/1984 | Sato et al. |
| 4,491,865 | A | 1/1985 | Danna et al. |
| 4,493,537 | A | 1/1985 | Nakahashi |
| 4,495,134 | A | 1/1985 | Ouchi et al. |
| 4,499,895 | A | 2/1985 | Takayama |
| 4,503,842 | A | 3/1985 | Takayama |
| 4,513,235 | A | 4/1985 | Acklam et al. |
| 4,515,444 | A | 5/1985 | Prescott et al. |
| 4,516,063 | A | 5/1985 | Kaye et al. |
| 4,519,391 | A | 5/1985 | Murakoshi |
| 4,552,130 | A | 11/1985 | Kinoshita |
| 4,559,928 | A | 12/1985 | Takayama |
| 4,566,437 | A | 1/1986 | Yamaguchi |
| 4,573,450 | A | 3/1986 | Arakawa |
| 4,580,210 | A | 4/1986 | Nordstrom |
| 4,586,923 | A | 5/1986 | Gould et al. |
| 4,615,330 | A | 10/1986 | Nagasaki et al. |
| 4,616,630 | A | 10/1986 | Arakawa |
| 4,617,915 | A | 10/1986 | Arakawa |
| 4,618,884 | A | 10/1986 | Nagasaki |
| 4,621,618 | A | 11/1986 | Omagari et al. |
| 4,622,584 | A | 11/1986 | Nagasaki et al. |
| 4,625,714 | A | 12/1986 | Toyota |
| 4,631,582 | A | 12/1986 | Nagasaki et al. |
| 4,633,303 | A | 12/1986 | Nagasaki et al. |
| 4,633,304 | A | 12/1986 | Nagasaki |
| 4,643,170 | A | 2/1987 | Miyazaki et al. |
| 4,646,723 | A | 3/1987 | Arakawa |
| 4,649,904 | A | 3/1987 | Krauter et al. |
| 4,651,202 | A | 3/1987 | Arakawa |
| 4,652,093 | A | 3/1987 | Stephen et al. |
| 4,652,916 | A | 3/1987 | Suzaki et al. |
| 4,654,701 | A | 3/1987 | Yabe |
| RE32,421 | E | 5/1987 | Hattori |
| 4,662,725 | A | 5/1987 | Nisioka |
| 4,663,657 | A | 5/1987 | Nagasaki et al. |
| 4,667,655 | A | 5/1987 | Ogiu et al. |
| 4,674,844 | A | 6/1987 | Nishioka et al. |
| 4,686,963 | A | 8/1987 | Cohen et al. |
| 4,697,210 | A | 9/1987 | Toyota et al. |
| 4,700,693 | A | 10/1987 | Lia et al. |
| 4,709,730 | A | 12/1987 | Zwilling |
| 4,714,075 | A | 12/1987 | Krauter et al. |
| 4,716,457 | A | 12/1987 | Matsuo |
| 4,719,508 | A | 1/1988 | Sasaki et al. |
| 4,727,417 | A | 2/1988 | Kanno et al. |
| 4,727,418 | A | 2/1988 | Kato et al. |
| 4,745,470 | A | 5/1988 | Yabe et al. |
| 4,745,471 | A | 5/1988 | Takamura et al. |
| 4,746,974 | A | 5/1988 | Matsuo |
| 4,748,970 | A | 6/1988 | Nakajima |
| 4,755,029 | A | 7/1988 | Okobe |
| 4,762,119 | A | 8/1988 | Allred et al. |
| 4,765,312 | A | 8/1988 | Sasa et al. |
| 4,766,489 | A | 8/1988 | Kato |
| 4,787,369 | A | 11/1988 | Allred et al. |
| 4,790,294 | A | 12/1988 | Allred et al. |
| 4,794,913 | A | 1/1989 | Shimonaka et al. |
| 4,796,607 | A | 1/1989 | Allred et al. |
| 4,800,869 | A | 1/1989 | Nakajima |
| 4,804,020 | A * | 2/1989 | Bartholomew ......... B29C 65/58 138/111 |
| 4,805,596 | A | 2/1989 | Hatori |
| 4,806,011 | A | 2/1989 | Bettinger |
| 4,816,909 | A | 3/1989 | Kimura et al. |
| 4,819,065 | A | 4/1989 | Eino |
| 4,819,077 | A | 4/1989 | Kikuchi et al. |
| 4,821,116 | A | 4/1989 | Nagasaki et al. |
| 4,824,225 | A | 4/1989 | Nishioka |
| 4,831,437 | A | 5/1989 | Nishioka et al. |
| 4,836,187 | A | 6/1989 | Iwakoshi et al. |
| 4,844,052 | A | 7/1989 | Iwakoshi et al. |
| 4,844,071 | A | 7/1989 | Chen et al. |
| 4,845,553 | A | 7/1989 | Konomura et al. |
| 4,845,555 | A | 7/1989 | Yabe et al. |
| 4,847,694 | A | 7/1989 | Nishihara |
| 4,853,772 | A | 8/1989 | Kikuchi |
| 4,860,731 | A | 8/1989 | Matsuura |
| 4,867,546 | A | 9/1989 | Nishioka et al. |
| 4,868,647 | A | 9/1989 | Uehara et al. |
| 4,869,237 | A | 9/1989 | Eino et al. |
| 4,873,965 | A | 10/1989 | Daniell |
| 4,875,468 | A | 10/1989 | Krauter et al. |
| 4,877,314 | A | 10/1989 | Kanamori |
| 4,882,623 | A | 11/1989 | Uchikubo |
| 4,884,134 | A | 11/1989 | Tsuji et al. |
| 4,885,634 | A | 12/1989 | Yabe |
| 4,890,159 | A | 12/1989 | Ogiu |
| 4,894,715 | A | 1/1990 | Uchikubo et al. |
| 4,895,431 | A | 1/1990 | Tsujiuchi et al. |
| 4,897,789 | A | 1/1990 | King et al. |
| 4,899,731 | A | 2/1990 | Takayama et al. |
| 4,899,732 | A | 2/1990 | Cohen |
| 4,899,787 | A | 2/1990 | Ouchi et al. |
| 4,905,666 | A | 3/1990 | Fukuka |
| 4,918,521 | A | 4/1990 | Yabe et al. |
| 4,919,112 | A | 4/1990 | Siegmund |
| 4,919,114 | A | 4/1990 | Miyazaki |
| 4,920,980 | A | 5/1990 | Jackowski |
| 4,928,172 | A | 5/1990 | Uehara et al. |
| 4,931,867 | A | 6/1990 | Kikuchi |
| 4,941,454 | A | 7/1990 | Wood et al. |
| 4,941,456 | A | 7/1990 | Wood et al. |
| 4,951,134 | A | 8/1990 | Nakasima et al. |
| 4,951,135 | A | 8/1990 | Sasagawa et al. |
| 4,952,040 | A | 8/1990 | Igarashi |
| 4,959,710 | A | 9/1990 | Uehara et al. |
| 4,960,127 | A | 10/1990 | Noce et al. |
| 4,961,110 | A | 10/1990 | Nakamura |
| 4,967,269 | A | 10/1990 | Sasagawa et al. |
| 4,971,034 | A | 11/1990 | Doi et al. |
| 4,973,311 | A | 11/1990 | Iwakoshi et al. |
| 4,979,497 | A | 12/1990 | Matsuura et al. |
| 4,982,725 | A | 1/1991 | Hibino et al. |
| 4,984,878 | A | 1/1991 | Miyano |
| 4,986,642 | A | 1/1991 | Yokota et al. |
| 4,987,884 | A | 1/1991 | Nishioka et al. |
| 4,989,075 | A | 1/1991 | Ito |
| 4,989,581 | A | 2/1991 | Tamburrino et al. |
| 4,996,974 | A | 3/1991 | Ciarlei |
| 4,996,975 | A | 3/1991 | Nakamura |
| 5,001,556 | A | 3/1991 | Nakamura et al. |
| 5,005,558 | A | 4/1991 | Aomori |
| 5,005,957 | A | 4/1991 | Kanamori et al. |
| 5,007,408 | A | 4/1991 | Ieoka |
| 5,018,509 | A | 5/1991 | Suzuki et al. |
| 5,022,382 | A | 6/1991 | Ohshoki et al. |
| 5,029,016 | A | 7/1991 | Hiyama et al. |
| 5,034,888 | A | 7/1991 | Uehara et al. |
| 5,040,069 | A | 8/1991 | Matsumoto et al. |
| RE33,689 | E | 9/1991 | Nishioka et al. |
| 5,045,935 | A | 9/1991 | Kikuchi |
| 5,049,989 | A | 9/1991 | Tsuji |
| 5,050,584 | A | 9/1991 | Matsuura |
| 5,050,974 | A | 9/1991 | Takasugi et al. |
| 5,056,503 | A | 10/1991 | Nagasaki |
| 5,061,994 | A | 10/1991 | Takahashi |
| 5,068,719 | A | 11/1991 | Tsuji |
| 5,069,254 | A * | 12/1991 | Vogelsang ............... F16L 9/19 138/111 |
| 5,074,861 | A | 12/1991 | Schneider et al. |
| 5,081,524 | A | 1/1992 | Tsuruoka et al. |
| 5,087,989 | A | 2/1992 | Igarashi |
| 5,110,645 | A | 5/1992 | Matsumoto et al. |
| 5,111,281 | A | 5/1992 | Sekiguchi |
| 5,111,306 | A | 5/1992 | Kanno et al. |

(56) References Cited

U.S. PATENT DOCUMENTS

| | | |
|---|---|---|
| 5,111,804 A | 5/1992 | Funakoshi |
| 5,113,254 A | 5/1992 | Kanno et al. |
| 5,116,310 A | 5/1992 | Seder et al. |
| 5,119,238 A | 6/1992 | Igarashi |
| 5,131,393 A | 7/1992 | Ishiguro et al. |
| 5,137,013 A | 8/1992 | Chiba et al. |
| 5,140,265 A | 8/1992 | Sakiyama et al. |
| 5,156,590 A | 10/1992 | Vilmar |
| 5,159,446 A | 10/1992 | Hibino et al. |
| 5,170,775 A | 12/1992 | Tagami |
| 5,172,225 A | 12/1992 | Takahashi et al. |
| 5,174,293 A | 12/1992 | Hagiwara |
| 5,176,629 A | 1/1993 | Kullas et al. |
| 5,190,520 A | 3/1993 | Fenton, Jr. et al. |
| 5,191,878 A | 3/1993 | Iida et al. |
| 5,198,931 A | 3/1993 | Igarashi |
| 5,201,908 A | 4/1993 | Jones |
| 5,208,702 A | 5/1993 | Shiraiwa |
| 5,209,220 A | 5/1993 | Hiyama et al. |
| 5,225,958 A | 7/1993 | Nakamura |
| 5,228,356 A | 7/1993 | Chuang |
| 5,243,416 A | 9/1993 | Nakazawa |
| 5,243,967 A | 9/1993 | Hibino |
| 5,257,628 A | 11/1993 | Ishiguro et al. |
| 5,271,381 A | 12/1993 | Ailinger et al. |
| RE34,504 E | 1/1994 | Uehara et al. |
| 5,291,010 A | 3/1994 | Tsuji |
| 5,299,559 A | 4/1994 | Bruce et al. |
| 5,311,858 A | 5/1994 | Adair |
| 5,325,845 A | 7/1994 | Adair et al. |
| 5,331,551 A | 7/1994 | Tsuruoka et al. |
| 5,342,299 A | 8/1994 | Snoke et al. |
| 5,347,989 A | 9/1994 | Monroe et al. |
| 5,358,011 A | 10/1994 | Stockton et al. |
| 5,374,953 A | 12/1994 | Sasaki et al. |
| 5,379,757 A | 1/1995 | Hiyama et al. |
| 5,381,782 A | 1/1995 | DeLaRama et al. |
| 5,390,662 A | 2/1995 | Okada |
| 5,400,769 A | 3/1995 | Tanii et al. |
| 5,402,768 A | 4/1995 | Adair |
| 5,402,769 A | 4/1995 | Tsuji |
| 5,409,485 A | 4/1995 | Suda |
| 5,412,478 A | 5/1995 | Ishihara et al. |
| 5,418,649 A | 5/1995 | Igarashi |
| 5,420,644 A | 5/1995 | Watanabe |
| 5,431,645 A | 7/1995 | Smith et al. |
| 5,434,615 A | 7/1995 | Matsumoto |
| 5,436,640 A | 7/1995 | Reeves |
| 5,436,767 A | 7/1995 | Suzuki et al. |
| 5,440,341 A | 8/1995 | Suzuki et al. |
| 5,464,007 A | 11/1995 | Krauter et al. |
| 5,469,840 A | 11/1995 | Tanii et al. |
| 5,473,235 A | 12/1995 | Lance et al. |
| 5,482,029 A | 1/1996 | Sekiguchi et al. |
| 5,484,407 A | 1/1996 | Osypka |
| 5,484,408 A | 1/1996 | Burns |
| 5,485,316 A | 1/1996 | Morl et al. |
| 5,496,260 A | 3/1996 | Krauter et al. |
| 5,515,449 A | 5/1996 | Tsuruoka et al. |
| 5,518,501 A | 5/1996 | Oneda et al. |
| 5,518,502 A | 5/1996 | Kaplan et al. |
| 5,543,831 A | 8/1996 | Tsuji et al. |
| 5,569,158 A | 10/1996 | Suzuki et al. |
| 5,569,159 A | 10/1996 | Anderson et al. |
| 5,569,195 A | 10/1996 | Saab |
| 5,586,262 A | 12/1996 | Komatsu et al. |
| 5,589,854 A | 12/1996 | Tsai |
| 5,591,202 A | 1/1997 | Slater et al. |
| 5,608,451 A | 3/1997 | Konno et al. |
| 5,609,574 A | 3/1997 | Kaplan et al. |
| 5,619,380 A | 4/1997 | Agasawa et al. |
| 5,622,528 A | 4/1997 | Hamano et al. |
| 5,631,695 A | 5/1997 | Nakamura et al. |
| 5,633,203 A | 5/1997 | Adair |
| 5,643,203 A | 7/1997 | Beiser et al. |
| 5,645,075 A | 7/1997 | Palmer et al. |
| 5,647,840 A | 7/1997 | D'Amelio et al. |
| 5,658,238 A | 8/1997 | Suzuki et al. |
| 5,667,477 A | 9/1997 | Segawa |
| 5,674,182 A | 10/1997 | Suzuki et al. |
| 5,674,197 A | 10/1997 | Van Muiden et al. |
| 5,685,823 A | 11/1997 | Ito et al. |
| 5,685,825 A | 11/1997 | Takase et al. |
| 5,691,853 A | 11/1997 | Miyano |
| 5,695,450 A | 12/1997 | Yabe et al. |
| 5,698,866 A | 12/1997 | Doiron et al. |
| 5,702,349 A | 12/1997 | Morizumi |
| 5,702,754 A | 12/1997 | Zhong |
| 5,703,724 A | 12/1997 | Miyano |
| 5,704,371 A | 1/1998 | Shepard |
| 5,704,896 A | 1/1998 | Fukunishi et al. |
| 5,708,482 A | 1/1998 | Takahashi et al. |
| 5,721,566 A | 2/1998 | Rosenberg et al. |
| 5,724,068 A | 3/1998 | Sanchez et al. |
| 5,728,045 A | 3/1998 | Komi |
| 5,739,811 A | 4/1998 | Rosenberg et al. |
| 5,740,801 A | 4/1998 | Branson |
| 5,746,696 A | 5/1998 | Kondo |
| 5,762,631 A | 6/1998 | Klein |
| 5,764,809 A | 6/1998 | Nomami et al. |
| 5,767,839 A | 6/1998 | Rosenberg |
| 5,779,673 A | 7/1998 | Roth et al. |
| 5,779,686 A | 7/1998 | Sato et al. |
| 5,781,172 A | 7/1998 | Engel et al. |
| 5,788,714 A | 8/1998 | Ouchi |
| 5,789,047 A | 8/1998 | Sasaki et al. |
| 5,793,539 A | 8/1998 | Konno et al. |
| 5,805,140 A | 9/1998 | Rosenberg et al. |
| 5,810,715 A | 9/1998 | Moriyama |
| 5,812,983 A | 9/1998 | Kumagai |
| 5,819,736 A | 10/1998 | Avny et al. |
| 5,820,591 A | 10/1998 | Thompson et al. |
| 5,821,466 A | 10/1998 | Clark et al. |
| 5,821,920 A | 10/1998 | Rosenberg et al. |
| 5,823,948 A | 10/1998 | Ross, Jr. et al. |
| 5,827,177 A | 10/1998 | Oneda et al. |
| 5,827,186 A | 10/1998 | Chen et al. |
| 5,827,190 A | 10/1998 | Palcic et al. |
| 5,828,197 A | 10/1998 | Martin et al. |
| 5,828,363 A | 10/1998 | Yaniger et al. |
| 5,830,124 A | 11/1998 | Suzuki et al. |
| 5,830,128 A | 11/1998 | Tanaka |
| 5,836,869 A | 11/1998 | Kudo et al. |
| 5,837,023 A | 11/1998 | Koike et al. |
| 5,840,014 A | 11/1998 | Miyano et al. |
| 5,841,126 A | 11/1998 | Fossum et al. |
| 5,843,000 A | 12/1998 | Nishioka et al. |
| 5,846,183 A | 12/1998 | Chilcoat |
| 5,855,560 A | 1/1999 | Idaomi et al. |
| 5,857,963 A | 1/1999 | Pelchy et al. |
| 5,865,724 A | 2/1999 | Palmer et al. |
| 5,868,664 A | 2/1999 | Speier et al. |
| 5,868,666 A | 2/1999 | Okada et al. |
| 5,873,816 A | 2/1999 | Kagawa et al. |
| 5,873,866 A | 2/1999 | Kondo et al. |
| 5,876,326 A | 3/1999 | Takamura et al. |
| 5,876,331 A | 3/1999 | Wu et al. |
| 5,876,373 A | 3/1999 | Giba et al. |
| 5,876,427 A | 3/1999 | Chen et al. |
| 5,877,819 A | 3/1999 | Branson |
| 5,879,284 A | 3/1999 | Tsujita |
| 5,880,714 A | 3/1999 | Rosenberg et al. |
| 5,882,293 A | 3/1999 | Ouchi |
| 5,882,339 A | 3/1999 | Beiser et al. |
| 5,889,670 A | 3/1999 | Schuler et al. |
| 5,889,672 A | 3/1999 | Schuler et al. |
| 5,892,630 A | 4/1999 | Broome |
| 5,895,350 A | 4/1999 | Hori |
| 5,897,507 A | 4/1999 | Kortenbach et al. |
| 5,897,525 A | 4/1999 | Dey et al. |
| 5,907,487 A | 5/1999 | Rosenberg et al. |
| 5,923,018 A | 7/1999 | Kameda et al. |
| 5,928,136 A | 7/1999 | Barry |
| 5,929,607 A | 7/1999 | Rosenberg et al. |

(56) References Cited

U.S. PATENT DOCUMENTS

| | | |
|---|---|---|
| 5,929,846 A | 7/1999 | Rosenberg et al. |
| 5,929,900 A | 7/1999 | Yamanaka |
| 5,929,901 A | 7/1999 | Adair et al. |
| 5,931,833 A | 8/1999 | Silverstein |
| 5,933,809 A | 8/1999 | Hunt et al. |
| 5,935,085 A | 8/1999 | Welsh et al. |
| 5,936,778 A | 8/1999 | Miyano et al. |
| 5,938,586 A | 8/1999 | Wilk et al. |
| 5,941,817 A | 8/1999 | Crawford |
| 5,947,953 A * | 9/1999 | Ash ................. A61M 25/0021 138/115 |
| 5,950,168 A | 9/1999 | Simborg et al. |
| 5,951,462 A | 9/1999 | Yamanaka |
| 5,956,416 A | 9/1999 | Tsuruoka et al. |
| 5,956,689 A | 9/1999 | Everhart |
| 5,956,690 A | 9/1999 | Haggerson et al. |
| 5,959,613 A | 9/1999 | Rosenberg et al. |
| 5,970,196 A | 10/1999 | Greveling et al. |
| 5,976,070 A | 11/1999 | Ono et al. |
| 5,976,074 A | 11/1999 | Moriyama |
| 5,980,454 A | 11/1999 | Broome |
| 5,980,468 A | 11/1999 | Zimmon |
| 5,986,693 A | 11/1999 | Adair et al. |
| 5,991,729 A | 11/1999 | Barry et al. |
| 5,991,730 A | 11/1999 | Lubin et al. |
| 5,999,168 A | 12/1999 | Rosenberg et al. |
| 6,002,425 A | 12/1999 | Yamanaka et al. |
| 6,007,482 A | 12/1999 | Madni et al. |
| 6,007,531 A | 12/1999 | Snoke et al. |
| 6,010,492 A | 1/2000 | Jacobsen et al. |
| 6,014,630 A | 1/2000 | Jeacock et al. |
| 6,015,088 A | 1/2000 | Parker et al. |
| 6,017,322 A | 1/2000 | Snoke et al. |
| 6,020,875 A | 2/2000 | Moore et al. |
| 6,020,876 A | 2/2000 | Rosenberg et al. |
| 6,026,363 A | 2/2000 | Shepard |
| 6,030,360 A | 2/2000 | Biggs |
| 6,032,120 A | 2/2000 | Rock et al. |
| 6,039,728 A | 3/2000 | Berlien et al. |
| 6,043,839 A | 3/2000 | Adair et al. |
| 6,050,718 A | 4/2000 | Schena et al. |
| 6,057,828 A | 5/2000 | Rosenberg et al. |
| 6,059,719 A | 5/2000 | Yamamoto et al. |
| 6,061,004 A | 5/2000 | Rosenberg |
| 6,067,077 A | 5/2000 | Martin et al. |
| 6,071,248 A | 6/2000 | Zimmon |
| 6,075,555 A | 6/2000 | Street |
| 6,078,308 A | 6/2000 | Rosenberg et al. |
| 6,078,353 A | 6/2000 | Yamanaka et al. |
| 6,078,876 A | 6/2000 | Rosenberg et al. |
| 6,080,104 A | 6/2000 | Ozawa et al. |
| 6,081,809 A | 6/2000 | Kumagai |
| 6,083,152 A | 7/2000 | Strong |
| 6,083,170 A | 7/2000 | Ben-Haim |
| 6,095,971 A | 8/2000 | Takahashi |
| 6,099,465 A | 8/2000 | Inoue |
| 6,099,513 A | 8/2000 | Spehalski |
| 6,100,874 A | 8/2000 | Schena et al. |
| 6,104,382 A | 8/2000 | Martin et al. |
| 6,120,435 A | 9/2000 | Eino |
| 6,125,337 A | 9/2000 | Rosenberg et al. |
| 6,128,006 A | 10/2000 | Rosenberg et al. |
| 6,132,369 A | 10/2000 | Takahashi |
| 6,134,056 A | 10/2000 | Nakamura |
| 6,134,506 A | 10/2000 | Rosenberg et al. |
| 6,135,946 A | 10/2000 | Konen et al. |
| 6,139,508 A | 10/2000 | Simpson et al. |
| 6,141,037 A | 10/2000 | Upton et al. |
| 6,142,956 A | 11/2000 | Kortenbach et al. |
| 6,146,355 A | 11/2000 | Biggs |
| 6,149,607 A | 11/2000 | Simpson et al. |
| 6,152,877 A | 11/2000 | Masters |
| 6,154,198 A | 11/2000 | Rosenberg |
| 6,154,248 A | 11/2000 | Ozawa et al. |
| 6,155,988 A | 12/2000 | Peters |
| 6,181,481 B1 | 1/2001 | Yamamoto et al. |
| 6,184,922 B1 | 2/2001 | Saito et al. |
| 6,193,714 B1 | 2/2001 | McGaffigan et al. |
| 6,195,592 B1 | 2/2001 | Schuler et al. |
| 6,203,493 B1 | 3/2001 | Ben-Haim |
| 6,206,824 B1 | 3/2001 | Ohara et al. |
| 6,211,904 B1 | 4/2001 | Adair |
| 6,216,104 B1 | 4/2001 | Moshfeghi et al. |
| 6,219,091 B1 | 4/2001 | Yamanaka et al. |
| 6,221,070 B1 | 4/2001 | Tu et al. |
| 6,238,799 B1 | 5/2001 | Opolski |
| 6,241,668 B1 | 6/2001 | Herzog |
| 6,260,994 B1 | 7/2001 | Matsumoto et al. |
| 6,272,470 B1 | 8/2001 | Teshima |
| 6,275,255 B1 | 8/2001 | Adair et al. |
| 6,283,960 B1 | 9/2001 | Ashley |
| 6,295,082 B1 | 9/2001 | Dowdy et al. |
| 6,299,625 B1 | 10/2001 | Bacher |
| 6,309,347 B1 | 10/2001 | Takahashi et al. |
| 6,310,642 B1 | 10/2001 | Adair et al. |
| 6,319,196 B1 | 11/2001 | Minami |
| 6,319,197 B1 | 11/2001 | Tsuji et al. |
| 6,334,844 B1 | 1/2002 | Akiba |
| 6,346,075 B1 | 2/2002 | Arai et al. |
| 6,358,200 B1 | 3/2002 | Grossi |
| 6,366,799 B1 | 4/2002 | Acker et al. |
| 6,381,029 B1 | 4/2002 | Tipirneni |
| 6,398,724 B1 | 6/2002 | May et al. |
| 6,413,207 B1 | 7/2002 | Minami |
| 6,421,078 B1 | 7/2002 | Akai et al. |
| 6,425,535 B1 | 7/2002 | Akiba |
| 6,425,858 B1 | 7/2002 | Minami |
| 6,436,032 B1 | 8/2002 | Eto et al. |
| 6,441,845 B1 | 8/2002 | Matsumoto |
| 6,447,444 B1 | 9/2002 | Avni et al. |
| 6,449,006 B1 | 9/2002 | Shipp |
| 6,453,190 B1 | 9/2002 | Acker et al. |
| 6,454,162 B1 | 9/2002 | Teller |
| 6,459,447 B1 | 10/2002 | Okada et al. |
| 6,468,204 B2 | 10/2002 | Sendai et al. |
| 6,475,141 B2 | 11/2002 | Abe |
| 6,478,730 B1 | 11/2002 | Bala et al. |
| 6,489,987 B1 | 12/2002 | Higuchi et al. |
| 6,496,827 B2 | 12/2002 | Kozam et al. |
| 6,498,948 B1 | 12/2002 | Ozawa et al. |
| 6,503,193 B1 | 1/2003 | Iwasaki et al. |
| 6,520,908 B1 | 2/2003 | Ikeda et al. |
| 6,524,234 B2 | 2/2003 | Ouchi |
| 6,530,882 B1 | 3/2003 | Farkas et al. |
| 6,533,722 B2 | 3/2003 | Nakashima |
| 6,540,669 B2 | 4/2003 | Abe et al. |
| 6,544,194 B1 | 4/2003 | Kortenbach et al. |
| 6,545,703 B1 | 4/2003 | Takahashi et al. |
| 6,551,239 B2 | 4/2003 | Renner et al. |
| 6,558,317 B2 | 5/2003 | Takahashi et al. |
| 6,561,971 B1 | 5/2003 | Akiba |
| 6,565,507 B2 | 5/2003 | Kamata et al. |
| 6,574,629 B1 | 6/2003 | Cooke, Jr. et al. |
| 6,589,162 B2 | 7/2003 | Nakashima et al. |
| 6,595,913 B2 | 7/2003 | Takahashi |
| 6,597,390 B1 | 7/2003 | Higuchi |
| 6,599,239 B2 | 7/2003 | Hayakawa et al. |
| 6,602,186 B1 | 8/2003 | Sugimoto et al. |
| 6,605,035 B2 | 8/2003 | Ando et al. |
| 6,609,135 B1 | 8/2003 | Omori et al. |
| 6,611,846 B1 | 8/2003 | Stoodley |
| 6,614,969 B2 | 9/2003 | Eichelberger et al. |
| 6,616,600 B2 * | 9/2003 | Pauker ................. A61B 1/00071 600/128 |
| 6,616,601 B2 | 9/2003 | Hayakawa |
| 6,623,424 B2 | 9/2003 | Hayakawa et al. |
| 6,638,214 B2 | 10/2003 | Akiba |
| 6,638,215 B2 | 10/2003 | Kobayashi |
| 6,641,528 B2 | 11/2003 | Torii |
| 6,651,669 B1 | 11/2003 | Burnside |
| 6,656,110 B1 | 12/2003 | Irion et al. |
| 6,656,112 B2 | 12/2003 | Miyanaga |
| 6,659,940 B2 | 12/2003 | Adler |
| 6,663,561 B2 | 12/2003 | Sugimoto et al. |

(56) References Cited

U.S. PATENT DOCUMENTS

| | | |
|---|---|---|
| 6,669,629 B2 | 12/2003 | Matsui |
| 6,673,012 B2 | 1/2004 | Fujii et al. |
| 6,677,984 B2 | 1/2004 | Kobayashi et al. |
| 6,678,397 B1 | 1/2004 | Omori et al. |
| 6,682,479 B1 | 1/2004 | Takahashi et al. |
| 6,685,631 B2 | 2/2004 | Minami |
| 6,686,949 B2 | 2/2004 | Kobayashi et al. |
| 6,690,409 B1 | 2/2004 | Takahashi |
| 6,690,963 B2 | 2/2004 | Ben-Haim et al. |
| 6,692,431 B2 | 2/2004 | Kazakevich |
| 6,697,101 B1 | 2/2004 | Takahashi et al. |
| 6,699,181 B2 | 3/2004 | Wako |
| 6,702,737 B2 | 3/2004 | Hino et al. |
| 6,711,426 B2 | 3/2004 | Benaron et al. |
| 6,715,068 B1 | 3/2004 | Abe |
| 6,716,162 B2 | 4/2004 | Hakamata |
| 6,728,599 B2 | 4/2004 | Wang et al. |
| 6,730,018 B2 | 5/2004 | Takase |
| 6,734,893 B1 | 5/2004 | Hess et al. |
| 6,736,773 B2 | 5/2004 | Wendlandt et al. |
| 6,743,240 B2 | 6/2004 | Smith et al. |
| 6,749,559 B1 | 6/2004 | Krass et al. |
| 6,749,560 B1 | 6/2004 | Konstorum et al. |
| 6,749,561 B2 | 6/2004 | Kazakevich |
| 6,753,905 B1 | 6/2004 | Okada et al. |
| 6,758,806 B2 | 7/2004 | Kamrava et al. |
| 6,758,807 B2 | 7/2004 | Minami |
| 6,758,842 B2 | 7/2004 | Irion et al. |
| 6,778,208 B2 | 8/2004 | Takeshige et al. |
| 6,780,151 B2 | 8/2004 | Grabover et al. |
| 6,785,410 B2 | 8/2004 | Vining et al. |
| 6,785,414 B1 | 8/2004 | McStravick et al. |
| 6,785,593 B2 | 8/2004 | Wang et al. |
| 6,796,938 B2 | 9/2004 | Sendai |
| 6,796,939 B1 | 9/2004 | Hirata et al. |
| 6,798,533 B2 | 9/2004 | Tipirneni |
| 6,800,056 B2 | 10/2004 | Tartaglia et al. |
| 6,800,057 B2 | 10/2004 | Tsujita et al. |
| 6,808,491 B2 | 10/2004 | Kortenbach et al. |
| 6,824,539 B2 | 11/2004 | Novak |
| 6,824,548 B2 | 11/2004 | Smith et al. |
| 6,829,003 B2 | 12/2004 | Takami |
| 6,830,545 B2 | 12/2004 | Bendall |
| 6,832,990 B2 | 12/2004 | Kortenbach et al. |
| 6,840,932 B2 | 1/2005 | Lang |
| 6,842,196 B1 | 1/2005 | Swift et al. |
| 6,846,286 B2 | 1/2005 | Suzuki et al. |
| 6,847,933 B1 | 1/2005 | Hastings |
| 6,849,043 B2 | 2/2005 | Kondo |
| 6,850,794 B2 | 2/2005 | Shahidi |
| 6,855,109 B2 | 2/2005 | Obata et al. |
| 6,858,004 B1 | 2/2005 | Ozawa et al. |
| 6,858,014 B2 | 2/2005 | Damarati |
| 6,860,849 B2 | 3/2005 | Matsushita et al. |
| 6,863,650 B1 | 3/2005 | Irion |
| 6,863,661 B2 | 3/2005 | Carrillo et al. |
| 6,868,195 B2 | 3/2005 | Fujita |
| 6,871,086 B2 | 3/2005 | Nevo et al. |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayahi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,821 B2 | 9/2005 | Abe et al. |
| 6,943,822 B2 | 9/2005 | Iida et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami et al. |
| 6,949,068 B2 | 9/2005 | Taniguchi et al. |
| 6,950,248 B2 | 9/2005 | Rudischhauser et al. |
| 6,950,691 B2 | 9/2005 | Uckikubo |
| 6,954,311 B2 | 10/2005 | Amanai |
| 6,955,671 B2 | 10/2005 | Uchikubo |
| 6,956,703 B2 | 10/2005 | Saito |
| 6,961,187 B2 | 11/2005 | Amanai |
| 6,962,564 B2 | 11/2005 | Hickle |
| 6,963,175 B2 | 11/2005 | Archenhold et al. |
| 6,964,662 B2 | 11/2005 | Kidooka et al. |
| 6,967,673 B2 | 11/2005 | Ozawa et al. |
| 6,974,466 B2 | 12/2005 | Ahmed et al. |
| 6,975,968 B2 | 12/2005 | Nakamitsu et al. |
| 6,976,954 B2 | 12/2005 | Takahashi |
| 6,977,053 B2 | 12/2005 | Mukasa et al. |
| 6,977,670 B2 | 12/2005 | Takahashi et al. |
| 6,980,227 B2 | 12/2005 | Iida et al. |
| 6,980,921 B2 | 12/2005 | Anderson et al. |
| 6,981,945 B1 | 1/2006 | Sarvazyan et al. |
| 6,982,740 B2 | 1/2006 | Adair et al. |
| 6,984,206 B2 | 1/2006 | Kumei et al. |
| 6,985,183 B2 | 1/2006 | Jan et al. |
| 6,986,686 B2 | 1/2006 | Shibata et al. |
| 6,994,668 B2 | 2/2006 | Miyano |
| 6,994,704 B2 | 2/2006 | Qin et al. |
| 7,001,330 B2 | 2/2006 | Kobayashi |
| 7,008,376 B2 | 3/2006 | Ikeda et al. |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0163575 A1 | 11/2002 | Ayame et al. |
| 2002/0193662 A1 | 12/2002 | Belson |
| 2002/0193664 A1 | 12/2002 | Ross et al. |
| 2003/0032863 A1 | 2/2003 | Kazakevich |
| 2003/0045778 A1 | 3/2003 | Ohline et al. |
| 2003/0065250 A1 | 4/2003 | Chiel et al. |
| 2003/0069897 A1 | 4/2003 | Roy et al. |
| 2003/0149338 A1 | 8/2003 | Francois et al. |
| 2003/0181905 A1 | 9/2003 | Long |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Meada et al. |
| 2004/0073085 A1 | 4/2004 | Ikeda et al. |
| 2004/0143159 A1 | 7/2004 | Wendlandt |
| 2004/0147809 A1 | 7/2004 | Kazakevich |
| 2004/0167379 A1 | 8/2004 | Akiba |
| 2004/0249247 A1 | 12/2004 | Iddan |
| 2004/0257608 A1 | 12/2004 | Tirpirneni |
| 2005/0006133 A1 | 1/2005 | Greiner et al. |
| 2005/0075626 A1* | 4/2005 | Venturelli ......... A61M 25/0012 |

(56) References Cited

U.S. PATENT DOCUMENTS

| | | | |
|---|---|---|---|
| | | | 604/524 |
| 2005/0192476 A1 | 9/2005 | Homan et al. | |
| 2005/0197861 A1 | 9/2005 | Omori et al. | |
| 2005/0200698 A1 | 9/2005 | Amling et al. | |
| 2005/0203341 A1* | 9/2005 | Welker et al. | 600/130 |
| 2005/0203418 A1 | 9/2005 | Yamada et al. | |
| 2005/0205958 A1 | 9/2005 | Taniguchi et al. | |
| 2005/0207645 A1 | 9/2005 | Nishimura et al. | |
| 2005/0209509 A1 | 9/2005 | Belson | |
| 2005/0225872 A1 | 10/2005 | Uzawa et al. | |
| 2005/0226508 A1 | 10/2005 | Gotohda | |
| 2005/0228221 A1 | 10/2005 | Hirakawa | |
| 2005/0228222 A1 | 10/2005 | Furumi | |
| 2005/0228227 A1 | 10/2005 | Weber | |
| 2005/0228697 A1 | 10/2005 | Funahashi | |
| 2005/0231591 A1 | 10/2005 | Abe | |
| 2005/0234507 A1 | 10/2005 | Geske et al. | |
| 2005/0243169 A1 | 11/2005 | Ono et al. | |
| 2005/0247081 A1 | 11/2005 | Sakata et al. | |
| 2005/0250983 A1 | 11/2005 | Tremaglio et al. | |
| 2005/0251112 A1 | 11/2005 | Danitz et al. | |
| 2005/0251998 A1 | 11/2005 | Bar-Or et al. | |
| 2005/0253044 A1 | 11/2005 | Kuriyama | |
| 2005/0256370 A1 | 11/2005 | Fujita | |
| 2005/0256373 A1 | 11/2005 | Bar-Or et al. | |
| 2005/0256377 A1 | 11/2005 | Deppmeier et al. | |
| 2005/0256424 A1 | 11/2005 | Zimmon | |
| 2005/0264687 A1 | 12/2005 | Murayama | |
| 2005/0267417 A1 | 12/2005 | Secrest et al. | |
| 2005/0271340 A1 | 12/2005 | Weisburg et al. | |
| 2005/0272978 A1 | 12/2005 | Brunnen et al. | |
| 2005/0273085 A1 | 12/2005 | Hinmane et al. | |
| 2005/0288545 A1 | 12/2005 | Matsumoto et al. | |
| 2005/0288553 A1 | 12/2005 | Sugimoto | |
| 2006/0015008 A1 | 1/2006 | Kennedy | |

FOREIGN PATENT DOCUMENTS

| | | |
|---|---|---|
| DE | 101 29 990 A1 | 1/2003 |
| EP | 0 075 153 B1 | 3/1983 |
| EP | 0 437 229 A1 | 7/1991 |
| EP | 0 689 851 A1 | 1/1996 |
| EP | 0 728 487 B1 | 8/1996 |
| EP | 1 300 883 A2 | 4/2003 |
| EP | 1 433 412 A1 | 6/2004 |
| JP | 58-78635 A | 5/1983 |
| JP | 05-31071 A2 | 2/1993 |
| JP | 05-091972 A2 | 4/1993 |
| JP | 06-105800 A2 | 4/1994 |
| JP | 06-254048 A2 | 9/1994 |
| JP | 07-8441 A2 | 1/1995 |
| JP | 10-113330 A2 | 5/1998 |
| JP | 10-286221 A2 | 10/1998 |
| JP | 11-216113 A2 | 8/1999 |
| JP | 2001-128933 A | 5/2001 |
| JP | 32-19521 B2 | 8/2001 |
| JP | 2002-007134 A | 1/2002 |
| JP | 2002-078675 A2 | 3/2002 |
| JP | 2002-102152 A2 | 4/2002 |
| JP | 2002-177197 A2 | 6/2002 |
| JP | 2002-185873 A2 | 6/2002 |
| JP | 2002-253481 A2 | 9/2002 |
| JP | 3372273 B2 | 11/2002 |
| JP | 2003-75113 A2 | 3/2003 |
| JP | 34-82238 B2 | 10/2003 |
| JP | 2005-253483 A | 9/2005 |
| WO | WO 93/13704 | 7/1993 |
| WO | WO 99/07301 A1 | 2/1999 |
| WO | WO 03/097156 A1 | 11/2003 |
| WO | WO 2004/016310 A2 | 2/2004 |
| WO | WO 2005/023082 A2 | 3/2005 |

* cited by examiner

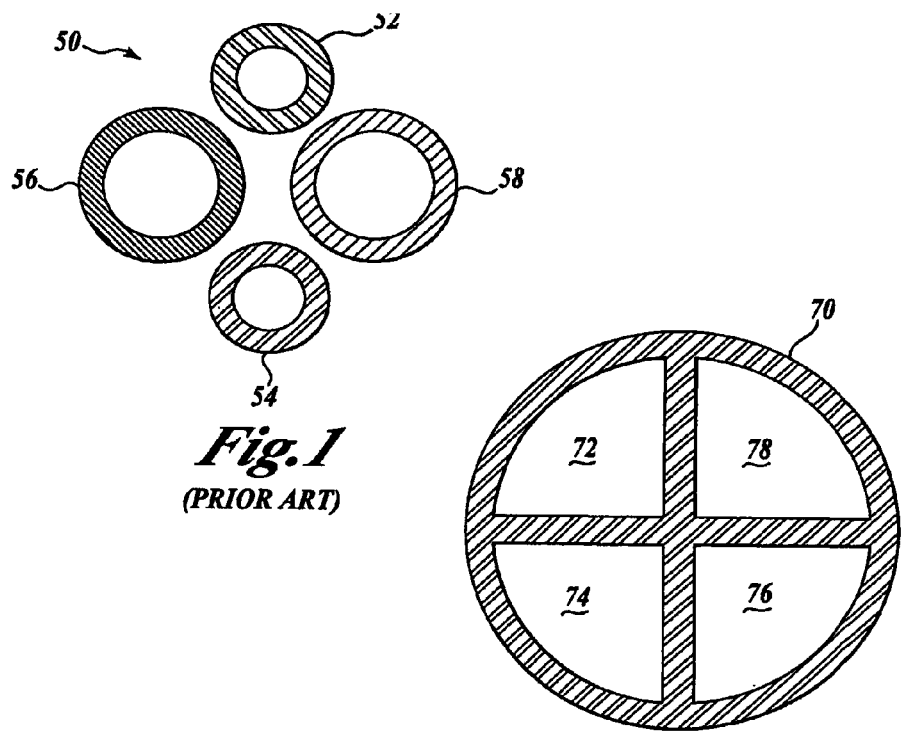
Fig.1
(PRIOR ART)
Fig.2A.
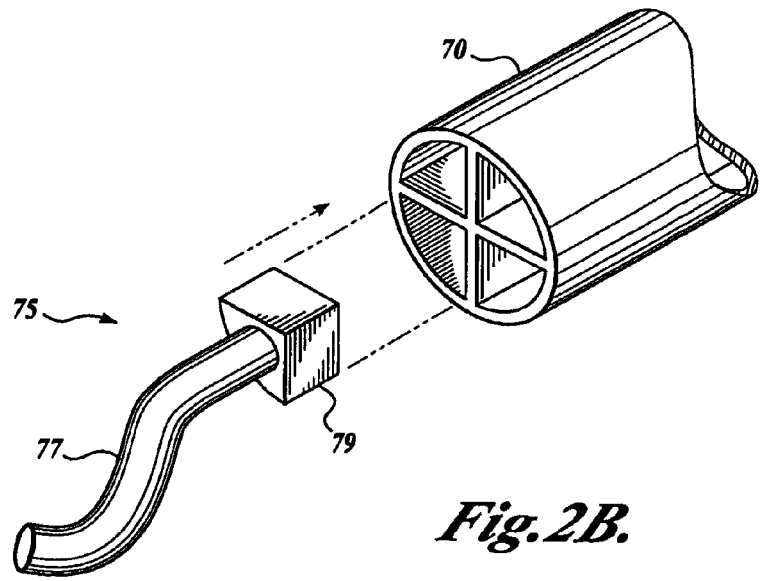
Fig.2B.

MULTIPLE LUMEN ASSEMBLY FOR USE IN ENDOSCOPES OR OTHER MEDICAL DEVICES

This application is a continuation of U.S. patent application Ser. No. 11/407,434, filed Apr. 20, 2006, the entire disclosure of which is incorporated herein by reference.

FIELD OF THE INVENTION

The present invention relates to medical devices, and in particular to endoscopes or other devices for inserting or retrieving items from a patient's body.

BACKGROUND OF THE INVENTION

Many endoscopes and other elongate medical devices that are designed to be advanced into the body include a shaft with one or more lumens therein. The lumens provide passageways between the distal and proximal ends of the shaft to direct air or water or surgical tools through the device. Alternatively, the lumens may be used to route internal components such as steering wires that selectively orient the distal tip of the device or electrical wires through the device.

One method of creating the lumens in the device is to insert individual tubes that form the lumens into the shaft. However, in order to keep the diameter of the device as small as possible, there is often little free space in the shaft for the tubes. As such, the tubes may bind or become wedged and difficult to advance through the shaft. Alternatively, the tubes may only fit in the shaft if they are arranged in a certain pattern, which is difficult to maintain as the tubes are incorporated into the shaft. Finally, by constructing the device using individual tubes for the lumens, it is generally necessary to keep a large inventory of tubes of various sizes at the location where such endoscopes or medical devices are assembled.

Given these problems, there is need for a medical device having multiple interior lumens that is more cost effective and easier to manufacture.

SUMMARY OF THE INVENTION

The present invention is a medical device such as an endoscope or catheter having an outer shaft and a lumen assembly with a number of individual lumens. Each of the lumens is interconnected such that the lumen assembly can be inserted as a group into the shaft.

In one embodiment, the lumens are formed from a tube having a number of individual passages or lumens formed therein. In another embodiment of the invention, the lumens comprise a series of tubes that are joined by a flexible sheet or web. The web may be continuous between the proximal and distal ends of the lumens. In another embodiment of the invention, the web may include a number of slots, cuts or other discontinuities between the proximal and distal ends.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 illustrates a number of conventional individual tubes that are placed within a shaft of an endoscope shaft or other medical device to create a number of corresponding lumens;

FIG. 2A illustrates one embodiment of a multiple lumen assembly for use in an endoscope or other medical device in accordance with one embodiment of the present invention;

FIG. 2B illustrates a lumen extension tube that can be used with the multiple lumen device shown in FIG. 2A;

DETAILED DESCRIPTION OF THE PREFERRED EMBODIMENT

Figure 2C:
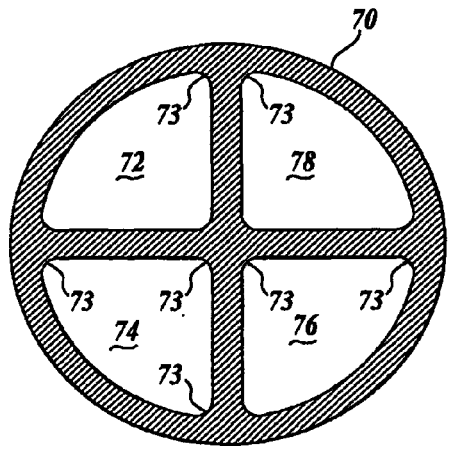
FIG. 2C illustrates further detail of the multiple lumen assembly shown in FIG. 2A.

As indicated above, the present invention is a multiple lumen assembly that can be incorporated into an endoscope shaft or other medical device.

FIG. 1 illustrates a conventional method of providing multiple lumens in an endoscope or other medical device. The multiple lumens 50 include a pair of smaller lumens 52, 54 that can be used for such functions as providing coolant to an LED or other light emitting device at the distal end of the endoscope. The coolant is delivered to the LEDs through a lumen 52 and returned to the proximal end of the device through the lumen 54. In addition, the multiple lumens include individual lumens 56 and 58. Lumen 56 may be used to provide a lens wash liquid to the distal tip, while lumen 58 can be used to provide insufflation gas to the distal tip. Each of the lumens 52, 54, 56, 58 may be made of an extruded tube of polymeric material. While such lumens are inexpensive to manufacture, they can be difficult to assemble within a shaft of the endoscope. The lumens may become lodged or kinked during insertion, or the lumens may become misaligned so that they do not fit within the interior of the shaft. Finally, the lumens take up space and limit shaft flexibility.

To overcome the problems associated with having to install individual tubes to create the lumens in the endoscope, the present invention is a multiple lumen assembly whereby individual lumen tubes are joined together for incorporation into an exterior shaft. In one embodiment of the invention shown in FIG. 2A, the multiple lumen assembly 70 comprises a single tube having a central lumen that is divided to create a number of smaller individual internal lumens 72, 74, 76, 78. The tube is preferably formed by an extrusion process to create the desired number of interior lumens within the tube. The lumen assembly 70 can then be advanced as a whole into an interior lumen of a surrounding shaft. Each of the lumens 72, 74, 76, 78 provides a passage for the delivery of materials, such as gases, liquids or tools through the endoscope.

In some instances, it is necessary to connect the individual lumens contained within the lumen assembly to another device such as a heat exchanger, or orifices at a distal end of the endoscope, etc. In that case, it may be necessary to employ a lumen extension such as that shown in FIG. 2B. Here, a lumen extension 75 includes a length of tubing material 77 and a plug 79. The plug 79 cooperates with the distal end of an individual lumen (e.g., lumen 74) contained within the lumen assembly 70 in order to connect the passageway of the individual lumen to the desired place. The lumen extension 75 allows for the passage of a liquid, air, or other material or device in the medical device.

FIG. 2C shows an additional advantage of an extruded lumen assembly such as the type shown in FIG. 2A. The lumen assembly 70 includes naturally rounded corners 73 within each of the individual lumens 72, 74, 76, 78. The rounded corners aid in preventing objects passed through the lumens from binding. The rounded corners 73 are a convenient by-product of an extruding process.

Figure 3:
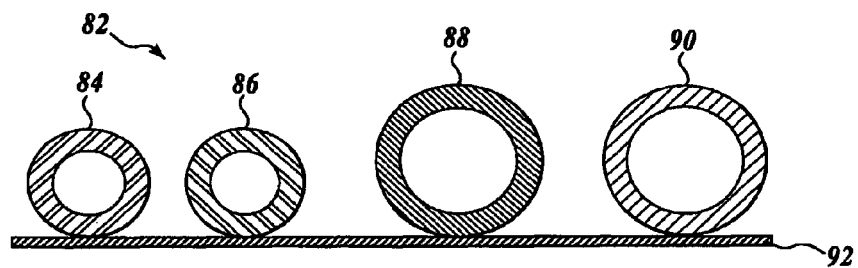
FIG. 3 illustrates a multiple lumen assembly having lumens held on a flexible strip in accordance with another embodiment of the present invention.

FIG. 3 illustrates an embodiment of the present invention whereby a multiple lumen assembly 82 includes a number of lumens 84, 86, 88, 90 that are formed of individual tubes. The tubes are formed with or secured to a sheet or strip of material 92. In this embodiment, the individual tubes that form the lumens can be formed separately and assembled into the lumen assembly 82 by securing them to the sheet or strip with an adhesive or the like. Alternatively, the lumens and the strip can be made as a single unit with an extrusion or molding process. Each of the tubes 84-90 is spaced apart on the strip 92 to allow the strip to be folded along its length for incorporation into an outer shaft of the endoscope or medical device.

Figure 4A:
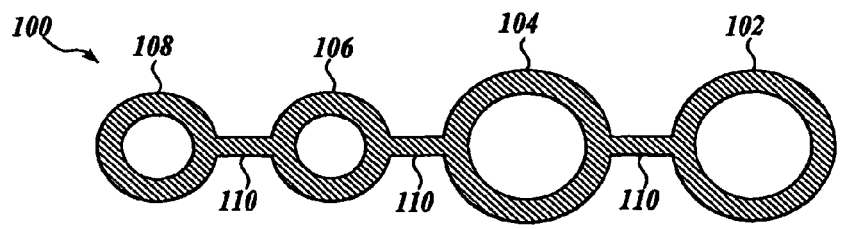
FIG. 4A illustrates another embodiment of a multiple lumen assembly in accordance with the present invention.

FIG. 4A illustrates another alternative embodiment of the multiple lumen assembly of the present invention. In this embodiment, a lumen assembly 100 is formed of a number of individual lumens 102, 104, 106, 108, etc., that are joined by a webbing material 110. The individual lumens 102-108 form a ribbon with the webbing material 110 positioned to join each of the adjacent lumens. In one embodiment, the multiple lumen assembly 100 is formed by an extrusion process. Each of the lumens 102-108 may be the same size or a different size, depending upon the intended purpose of the lumen.

Figure 4B:
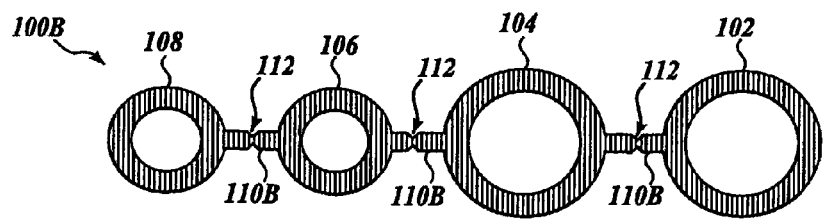
FIG. 4B illustrates another embodiment of a multiple lumen assembly in accordance with the present invention.

FIG. 4B illustrates another embodiment of the multiple lumen assembly shown in FIG. 4A. In this example, the multiple lumen assembly 100B comprises a series of lumens 102, 104, 106, 108 that are joined by a webbing material 110B. The webbing material 110B that joins adjacent lumens includes a pair of opposing notches 112 extending along the length thereof. The notches 112 aid in bending the webbing material such that the lumen assembly 100B can be folded for incorporation into the shaft of an endoscope or other medical device. In addition, the notches 112 aid in allowing the webbing material to be split so that individual lumens can be separated from the lumen assembly. Although the embodiment shown in FIG. 4B illustrates a single pair of notches 112 in the webbing material extending between adjacent lumens, it will be appreciated that additional notches or other flexibility enhancing mechanisms such as folds, etc., could be provided.

Figure 4C:
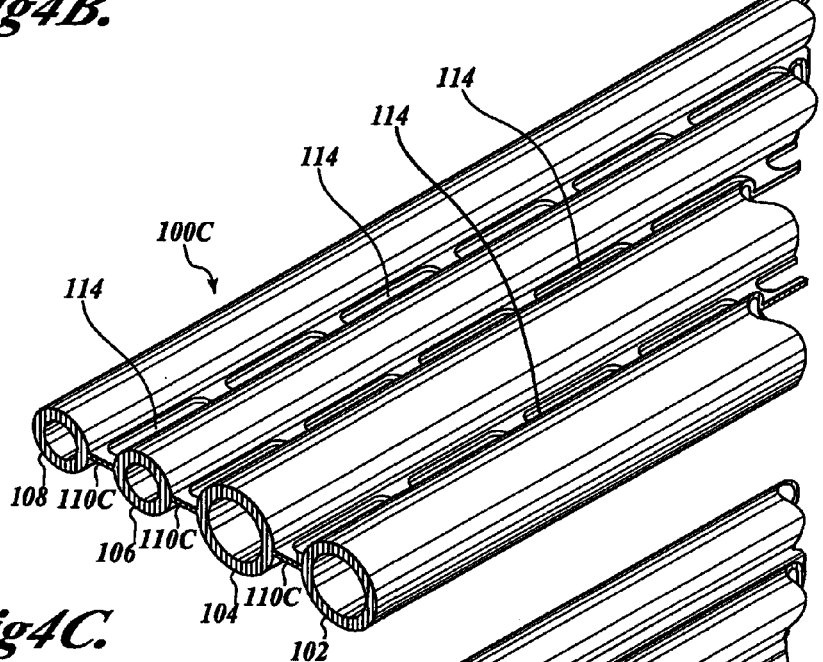
FIG. 4C illustrates one embodiment of a multiple lumen assembly having slots in a web that joins adjacent lumens in accordance with the present invention.

FIG. 4C illustrates yet another embodiment of the present invention wherein a lumen assembly 100C includes a number of individual lumens 102, 104, 106, 108 that are joined by a webbing material 110C. In this embodiment, the webbing material 110C includes a number of longitudinally extending slots 114 that are cut through the webbing material to increase the flexibility of the webbing material and allow individual lumens to be separated from the assembly. The slots may be formed with a laser after the lumen assembly is extruded or could be formed by other mechanisms such as with a knife. Although the slots 114 are illustrated as being generally oval in shape, it will be appreciated that the slots or holes could be other shapes, such as circular, rectangle, square, triangular, serpentine, etc.

Figure 4D:
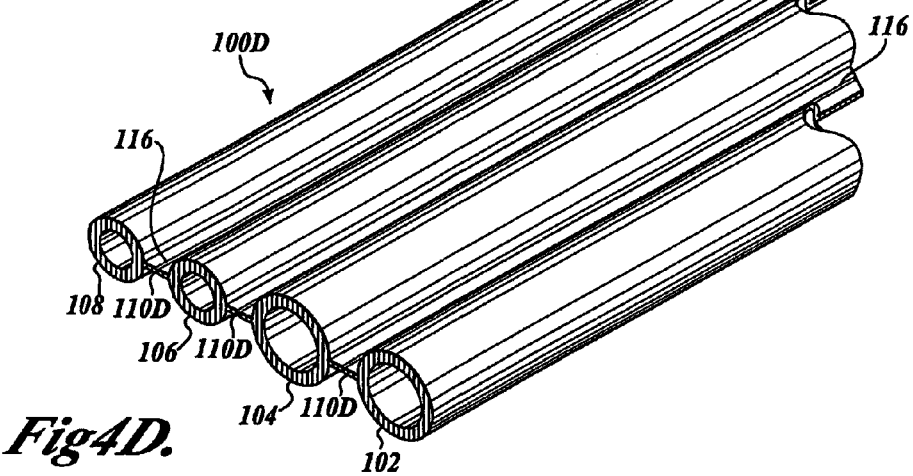
FIG. 4D illustrates a multiple lumen assembly having slits in the web joining adjacent lumens in accordance with another embodiment of the present invention.

FIG. 4D illustrates yet another alternative embodiment of a lumen assembly according to the present invention. The lumen assembly includes a number of individual lumens 102, 104, 106, 108 that are joined by a webbing material 110D. In this example, the webbing material 110D includes a number of longitudinally extending cuts 116 that extend entirely or partially through the webbing material. The cuts 116 aid in increasing the flexibility of the webbing material and allow the individual lumens to be separated by peeling individual lumens away from the lumen assembly. The individual lumens can then be connected to their appropriate destination. Furthermore, after the lumens are separated from the lumen assembly, they can be cut to the appropriate length.

Figure 5:
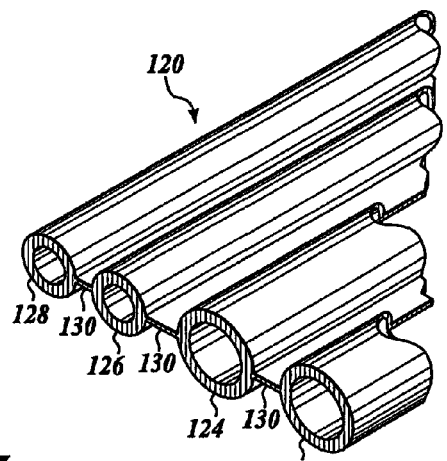
FIG. 5 illustrates a multiple lumen assembly having a web made of a different material that is different from the material that forms the lumens, in accordance with an embodiment of the present invention.

FIG. 5 shows yet another alternative embodiment of the present invention. In this embodiment, a multiple lumen assembly 120 comprises individual extruded lumens 122, 124, 126, 128 that are joined by a flexible webbing material 130. In the embodiment shown, the webbing material 130 may have a durometer value which is different from the durometer values of one or more of the individual lumens 122, 124, 126, 128. Furthermore, the durometer values of the individual lumens might not necessarily be the same, depending upon the purpose of the lumen. By making the durometer value of the webbing material 130 softer than the durometer of the individual lumens, the lumen bundle 120 becomes flexible in the longitudinal direction so that it can be folded for incorporation into the shaft of an endoscope or other medical device.

Figure 6:
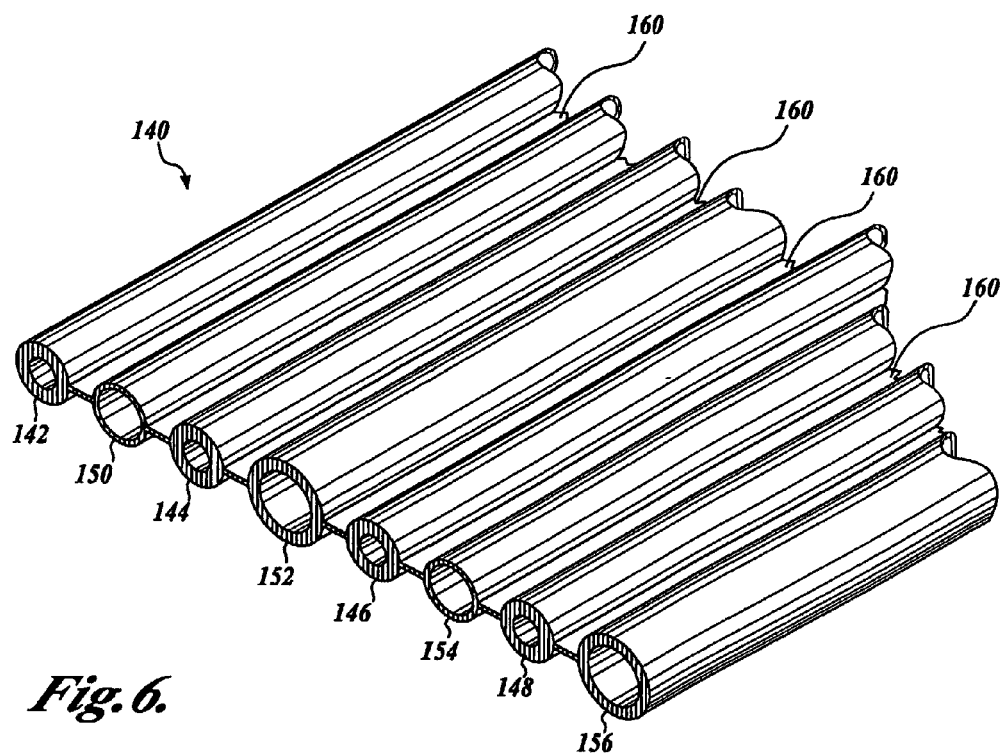
FIG. 6 illustrates a multiple lumen assembly including lumens that form the outer sheaths of Bowden cables in accordance with an embodiment of the present invention.

FIG. 6 illustrates another embodiment of the present invention. In this example, a multiple lumen assembly 140 includes a number of lumens 142, 144, 146, and 148 that are designed to function as the outer, thinner, sheath of a Bowden cable and are thicker or more rigid than the other lumens of the assembly. Positioned between the Bowden cable lumens are additional lumens 150, 152, 154, 156, which may be used to supply a cooling liquid or gas to an illumination light source such as one or more LEDs. In addition, the lumens 150-156 may be used to supply insufflation gas or a lens wash liquid to a distal end of the endoscope. Each of the lumens 142-156 is joined by a flexible webbing material 160 that extends between adjacent lumens to join them together into a flexible ribbon. One advantage of the multiple lumen assembly 140 is that the lumens can be arranged in any desired order such that when the lumen assembly is folded or rolled up for incorporation into an outer shaft of an endoscope, the individual lumens retain their orientation as they are advanced into the shaft. The orientation is preferably selected to minimize the amount of space occupied by the lumen assembly.

Figure 7A:
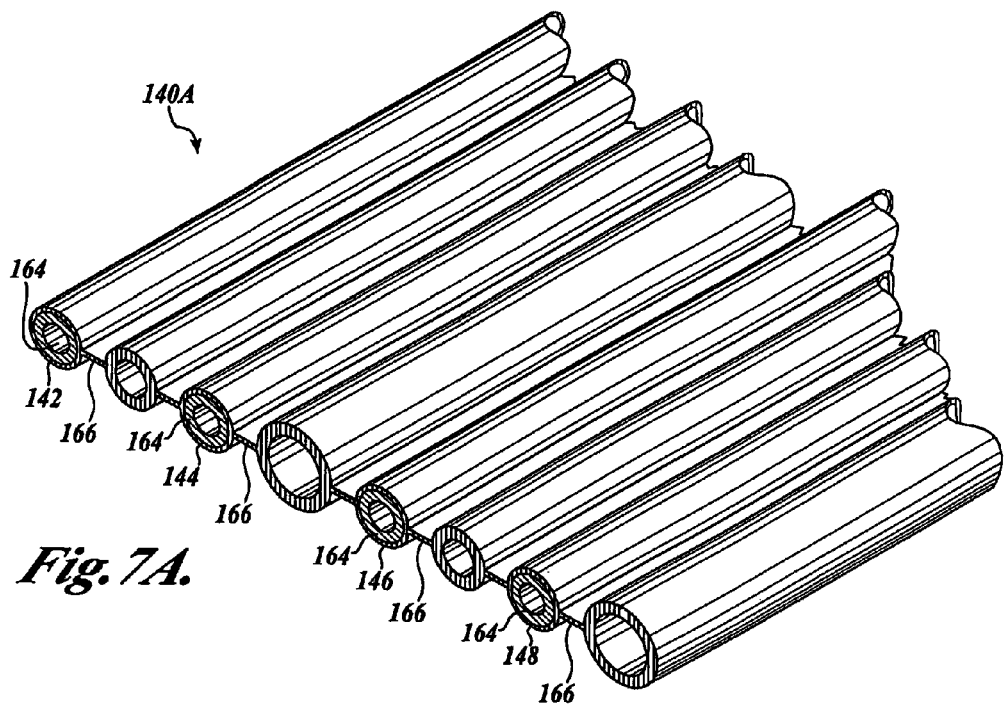
FIG. 7A illustrates further details of the lumens that form the outer sheaths of Bowden cables.

In one embodiment of the invention, each of the individual lumens is extruded from a single material. However, as shown in FIG. 7A, some of the lumens, such as the Bowden cable lumens 142, 144, 146, 148, may be extruded using two or more materials. For example, the Bowden cable lumens may include an inner layer 164 formed of a lubricious material such as HDPE. The inner layer 164 is covered with an outer layer 166, which may be formed of a different material. The outer layer 166 may also be used to form the webbing material that joins adjacent lumens. The inner layer 164 provides a slippery surface for the Bowden cables such that they do not bind under tension in order to steer the distal tip of an endoscope or medical device in a desired direction.

Figure 7B:
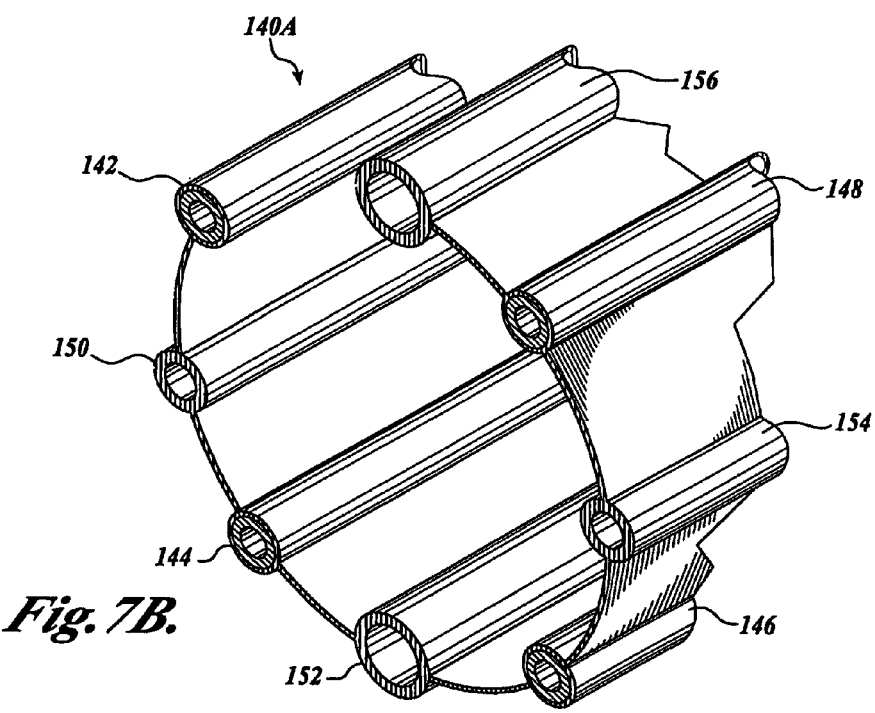
FIG. 7B illustrates a multiple lumen assembly that is folded for incorporation into a shaft.

FIG. 7B illustrates a lumen assembly 140A in a rolled or folded position for incorporation into an endoscope shaft (not shown). As will be appreciated, the free ends between the outer-most lumens 142, 156 of the lumen assembly are brought adjacent each other to facilitate the introduction of the lumens into the shaft. Furthermore, the assembly may be wrapped around an additional central lumen that forms a working channel of a device such as that shown in FIG. 7C. In the embodiment of the invention shown in FIG. 7C, a central lumen 170 extends through the center of the folded lumen assembly 140A. The central lumen 170 may form the working channel of the endoscope or other medical device. Once the lumen bundle 140A is wrapped around the central lumen 170, the combination can be advanced into an outer sheath in order to assemble the endoscope or other medical device.

Figure 7C:
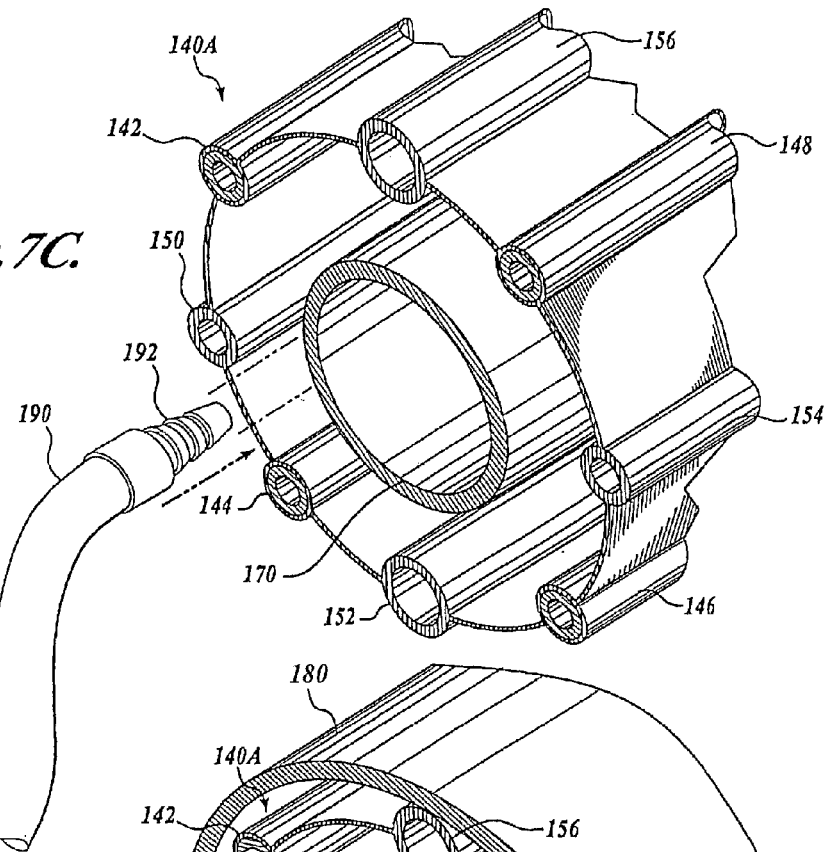
FIG. 7C illustrates a multiple lumen assembly that is wrapped around a central working channel lumen.
Figure 7D:
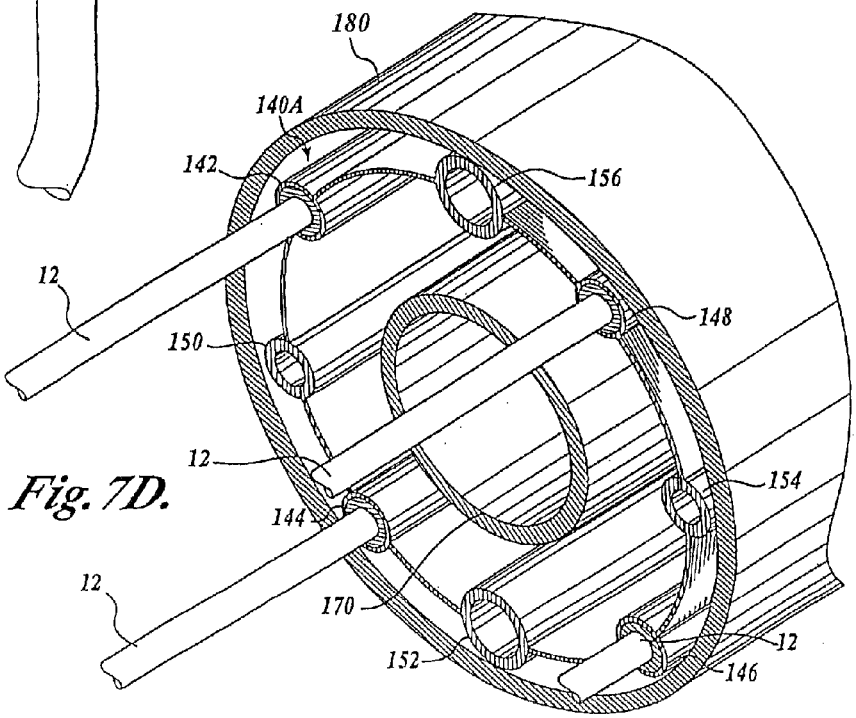
FIG. 7D illustrates a working channel and multiple lumen assembly positioned within an exterior shaft in accordance with an embodiment of the present invention.

FIG. 7D illustrates the lumen assembly 140A and the central lumen 170 in position with an outer shaft 180 of an endoscope. Once the lumen assembly 140A and central lumen 170 have been advanced to the distal end of the shaft, the individual lumens can be separated from the ribbon assembly and connected as desired. In addition, individual lumens from the lumen assembly can be trimmed to the appropriate length, as necessary. Alternatively, it may be necessary to attach a lumen extension 190 as shown in FIG. 7C to one or more individual lumens of the lumen assembly in order to connect the lumens to their desired locations. The lumen extension 190 includes a length of flexible tubing and a connector 192 that joins the flexible tubing to a lumen of the lumen assembly.

As will be appreciated, the present invention provides a simplified method for inserting multiple lumens within a medical device in order to both save space and to maintain the orientations of the lumens with respect to each other as they are positioned in an outer shaft. While the preferred embodiment of the invention has been illustrated and described, it will be appreciated that various changes can be made therein without departing from the scope of the invention. Therefore, the scope of the invention is to be determined from the following claims and equivalents thereof.

The embodiments of the invention in which an exclusive property or privilege is claimed are defined as follows:

1. A multi-lumen assembly, comprising:
    an outer shaft configured for insertion into a natural body lumen of a patient and having a central opening defining a first diameter;
    a flexible sheet of material configured to transition between a first planar configuration and a second configuration, wherein, in the first configuration, the flexible sheet of material defines a width larger than the first diameter and the flexible sheet of material includes a single, flat region connecting a first circular portion and a second circular portion, and when in the second configuration, the flexible sheet of material defines a width smaller than the first diameter and is configured to be received within the central opening; and
    a plurality of lumens fixedly attached to the sheet of material and configured to be received within the central opening.

2. The multi-lumen assembly of claim 1, wherein each of the plurality of lumens is adhesively secured to the sheet of material.

3. The multi-lumen assembly of claim 1, wherein each of the plurality of lumens is extruded as a one-piece assembly with the sheet of material.

4. The multi-lumen assembly of claim 1, wherein the sheet of material includes a number of perforations.

5. The multi-lumen assembly of claim 1, wherein the sheet of material includes a notch that penetrates less than an entire thickness of the sheet of material.

6. The multi-lumen assembly of claim 1, wherein at least one of the plurality of lumens is formed of a material different than a material of at least one other of the plurality of lumens.

7. The multi-lumen assembly of claim 1, wherein at least one of the plurality of lumens is formed of a material different than a material of the sheet of material.

8. The multi-lumen assembly of claim 1, further including:
    a working channel lumen surrounded by the sheet of material and configured to be received within the central opening.

9. The multi-lumen assembly of claim 1, further comprising:
    a lumen extension configured to cooperate with at least one of the plurality of lumens.

10. The multi-lumen assembly of claim 9, wherein the lumen extension includes a plug configured to be operatively coupled to a distal end portion of the at least one of the plurality of lumens.

11. The multi-lumen assembly of claim 10, further including a length of tubing extending from the plug.

12. The multi-lumen assembly of claim 1, wherein at least some of the plurality of lumens include an internal diameter larger than an internal diameter of each of a remainder of the plurality of lumens.

13. The multi-lumen assembly of claim 1, wherein at least some of the plurality of lumens include an inner layer and an outer layer, and the inner layer is formed of a first material and the outer layer is formed of a second material different than the first material.

14. The multi-lumen assembly of claim 1, wherein a portion of the sheet of material disposed in between adjacent lumens of the plurality of lumens includes a longitudinally extending cut.

15. The multi-lumen assembly of claim 14, wherein the longitudinally extending cut extends only partially through a thickness of the sheet of material.

16. The multi-lumen assembly of claim 1, wherein the sheet of material includes a durometer value different than a durmoeter value of a wall of one of the plurality of lumens.

17. The multi-lumen assembly of claim 1, wherein a durometer value of a wall of one of the plurality of lumens is different than a durometer value of a wall of another one of the plurality of lumens.

18. A multi-lumen assembly, comprising:
    an outer shaft configured for insertion into a natural body lumen of a patient and having a central opening defining a first diameter; and
    a plurality of lumens fixedly attached to a flexible sheet of material and configured to be received within the central opening;
    wherein the flexible sheet of material is configured to transition between a first planar configuration and a second configuration, wherein, in the first configuration, the flexible sheet of material defines a width larger than the first diameter and, when in the second configuration, the flexible sheet of material defines a width smaller than the first diameter, is configured to be received within the central opening, and is configured so that an outermost surface of the plurality of lumens protrudes into the central opening further than a portion of the flexible sheet of material disposed between adjacent lumens, and wherein a first lumen of the plurality of lumens is circular and includes a first outer diameter and a second lumen of the plurality of lumens is circular and includes a second outer diameter different than the first outer diameter.

19. The multi-lumen assembly of claim 18, wherein when the flexible sheet of material is in the second configuration, the plurality of lumens contact the portion of the sheet of material disposed between adjacent lumens at a location the plurality of lumens are fixedly attached.

20. A multi-lumen assembly, comprising:
an outer shaft configured for insertion into a natural body lumen of a patient and having a central opening defining a first diameter;
a flexible sheet of material configured to transition between a first planar configuration and a second configuration, wherein, in the first configuration, the flexible sheet of material defines a width larger than the first diameter and, when in the second configuration, the flexible sheet of material defines a width smaller than the first diameter and is configured to be received within the central opening;
a plurality of lumens fixedly attached to the flexible sheet of material and configured to be received within the central opening, wherein the flexible sheet of material includes two free ends and in the first configuration each of the free ends is one of the plurality of lumens; and
a working channel lumen surrounded by the flexible sheet of material and configured to be received within the central opening, wherein when the flexible sheet of material is in the second configuration, a gap is located between the working channel lumen and the flexible sheet of material.

* * * * *